United States Patent
Mochizuki

(10) Patent No.: US 10,471,202 B2
(45) Date of Patent: Nov. 12, 2019

(54) BLOOD PURIFICATION APPARATUS

(71) Applicant: Nikkiso Company Limited, Tokyo (JP)

(72) Inventor: Hiroaki Mochizuki, Shizuoka (JP)

(73) Assignee: Nikkiso Company Limited, Tokyo (JP)

(*) Notice: Subject to any disclaimer, the term of this patent is extended or adjusted under 35 U.S.C. 154(b) by 408 days.

(21) Appl. No.: 15/343,652

(22) Filed: Nov. 4, 2016

(65) Prior Publication Data

US 2017/0072126 A1 Mar. 16, 2017

Related U.S. Application Data

(63) Continuation of application No. PCT/JP2015/063783, filed on May 13, 2015.

(30) Foreign Application Priority Data

May 13, 2014 (JP) ................................ 2014-099857

(51) Int. Cl.
*A61M 1/36* (2006.01)
*A61M 1/16* (2006.01)
(Continued)

(52) U.S. Cl.
CPC .............. *A61M 1/367* (2013.01); *A61M 1/14* (2013.01); *A61M 1/1621* (2014.02);
(Continued)

(58) Field of Classification Search
CPC .... A61M 1/14; A61M 1/1601; A61M 1/1621; A61M 1/1643; A61M 1/34; A61M 1/367;
(Continued)

(56) References Cited

U.S. PATENT DOCUMENTS

2004/0154966 A1* 8/2004 Meziere .................. A61M 1/16
210/85
2010/0094194 A1 4/2010 Peters et al.
2010/0315231 A1* 12/2010 Rada ....................... A61M 1/16
340/540

FOREIGN PATENT DOCUMENTS

JP  H11-128342 A  5/1999
JP  2008000318 A  1/2008
(Continued)

OTHER PUBLICATIONS

International Search Report from the Japanese Patent Office for Application No. PCT/JP2015/063783, dated Aug. 11, 2015.
(Continued)

*Primary Examiner* — Benjamin J Klein
(74) *Attorney, Agent, or Firm* — Young Basile Hanlon & MacFarlane, P.C.

(57) ABSTRACT

The present teachings provide a blood purification apparatus in which inadvertent replacement of a container bag attached to a hanger portion can be avoided the blood purification apparatus including a holding device capable of holding a container bag that contains a liquid for blood purification treatment, such as dialysate, substitution fluid, or anticoagulant, the blood purification apparatus being capable of performing blood purification treatment using the liquid in the container bag, and the holding device including a hanger portion including an attachment portion to which the container bag can be attached, and movable between a use position and a replacement position, a measuring device capable of measuring the weight of the container bag held by the hanger portion, and a restricting device that restricts attachment and detachment of the container bag to and from the attachment portion when the hanger portion is in the use position.

20 Claims, 17 Drawing Sheets

(51) Int. Cl.
*A61M 1/34* (2006.01)
*A61M 1/14* (2006.01)
*A61M 5/14* (2006.01)
*A61M 5/168* (2006.01)
*F16B 45/02* (2006.01)

(52) U.S. Cl.
CPC ............ *A61M 1/1643* (2014.02); *A61M 1/34* (2013.01); *A61M 5/1417* (2013.01); *A61M 5/16845* (2013.01); *A61M 1/1601* (2014.02); *A61M 5/14* (2013.01); *A61M 2205/18* (2013.01); *A61M 2205/276* (2013.01); *A61M 2205/3393* (2013.01); *A61M 2209/082* (2013.01); *A61M 2209/084* (2013.01); *F16B 45/02* (2013.01)

(58) Field of Classification Search
CPC ............ A61M 5/1414; A61M 2205/14; A61M 2209/082; A61M 2209/084; F16B 45/02
See application file for complete search history.

(56) References Cited

FOREIGN PATENT DOCUMENTS

| | | |
|---|---|---|
| JP | 2009131595 A | 6/2009 |
| WO | 2004/069312 A1 | 8/2004 |
| WO | 2006/037429 A1 | 4/2006 |

OTHER PUBLICATIONS

Written Opinion from the Japanese Patent Office for Application No. PCT/JP2015/063783, dated Aug. 11, 2015.
Copending U.S. Appl. No. 15/292,404, filed Oct. 13, 2016.

* cited by examiner

[Fig 1]
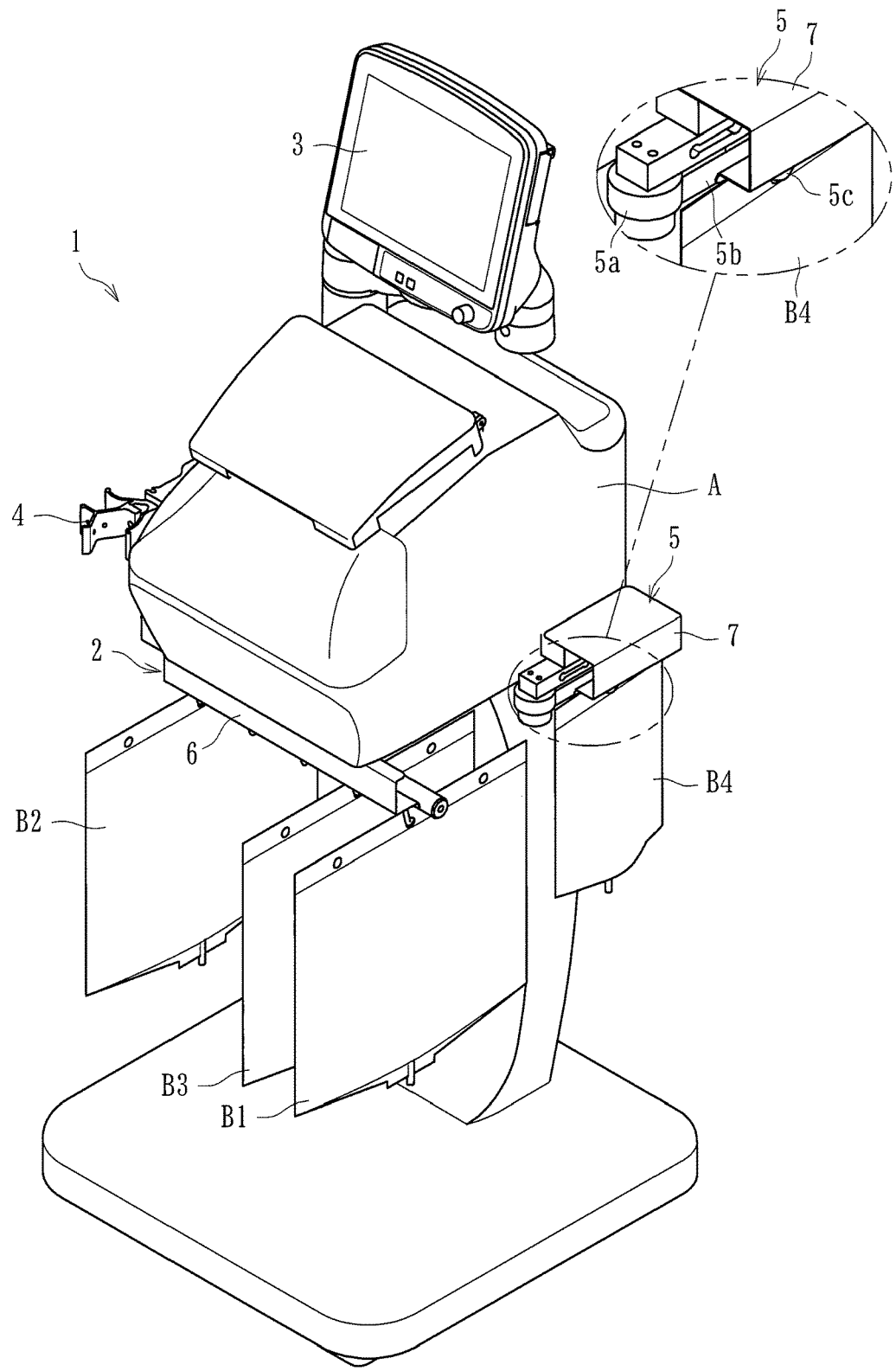

[Fig 2]
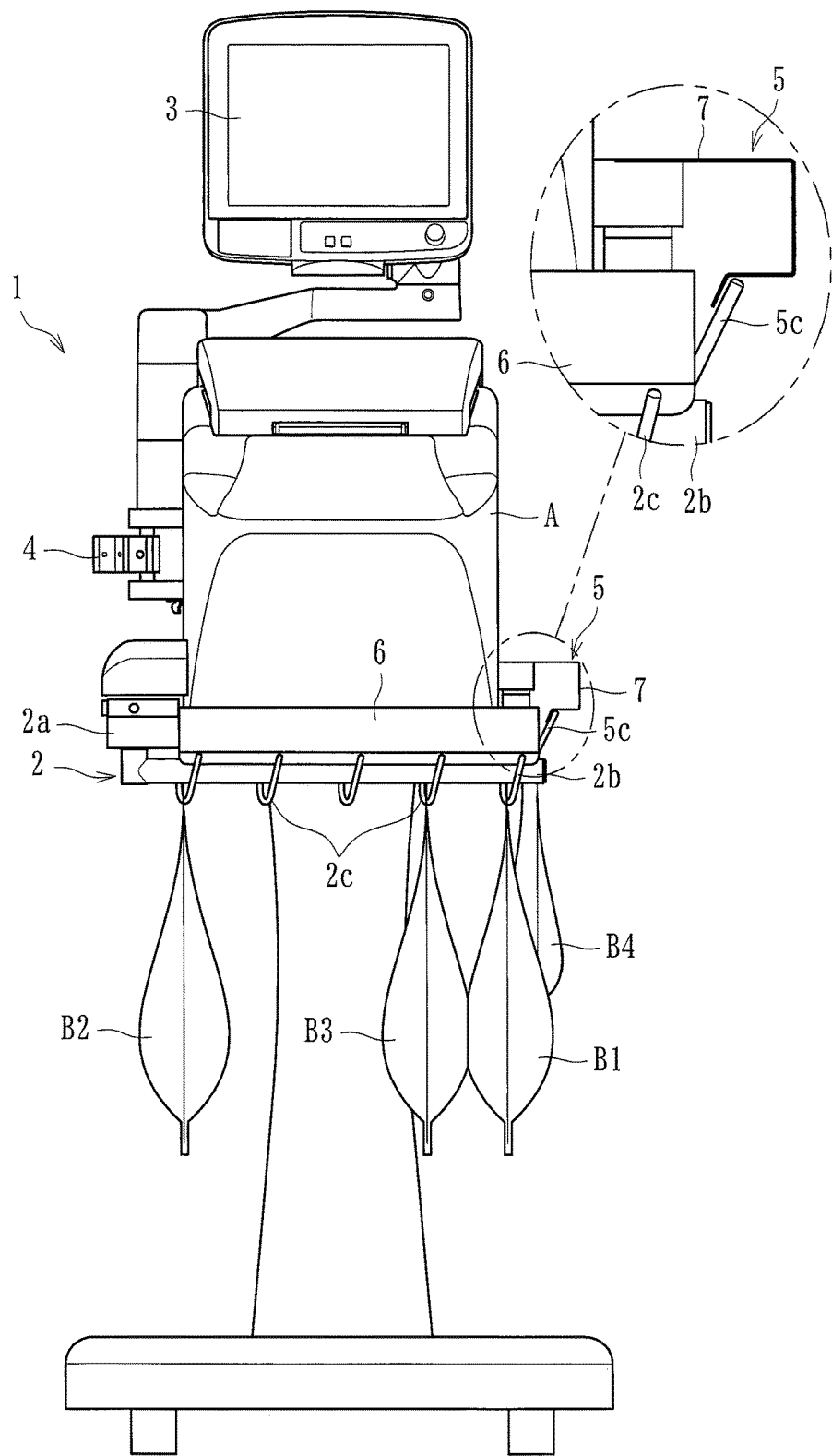

[Fig 3]
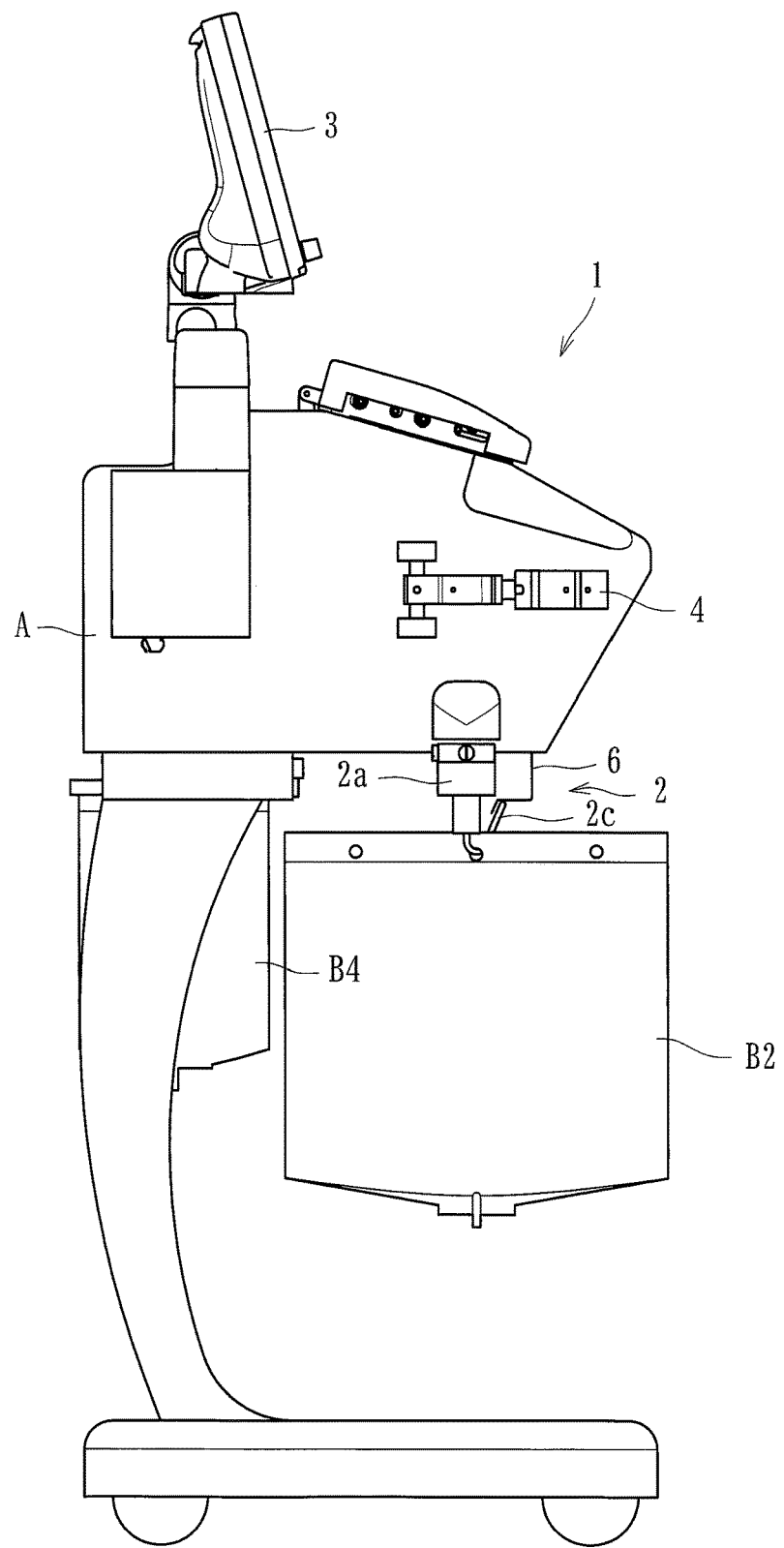

[Fig 4]
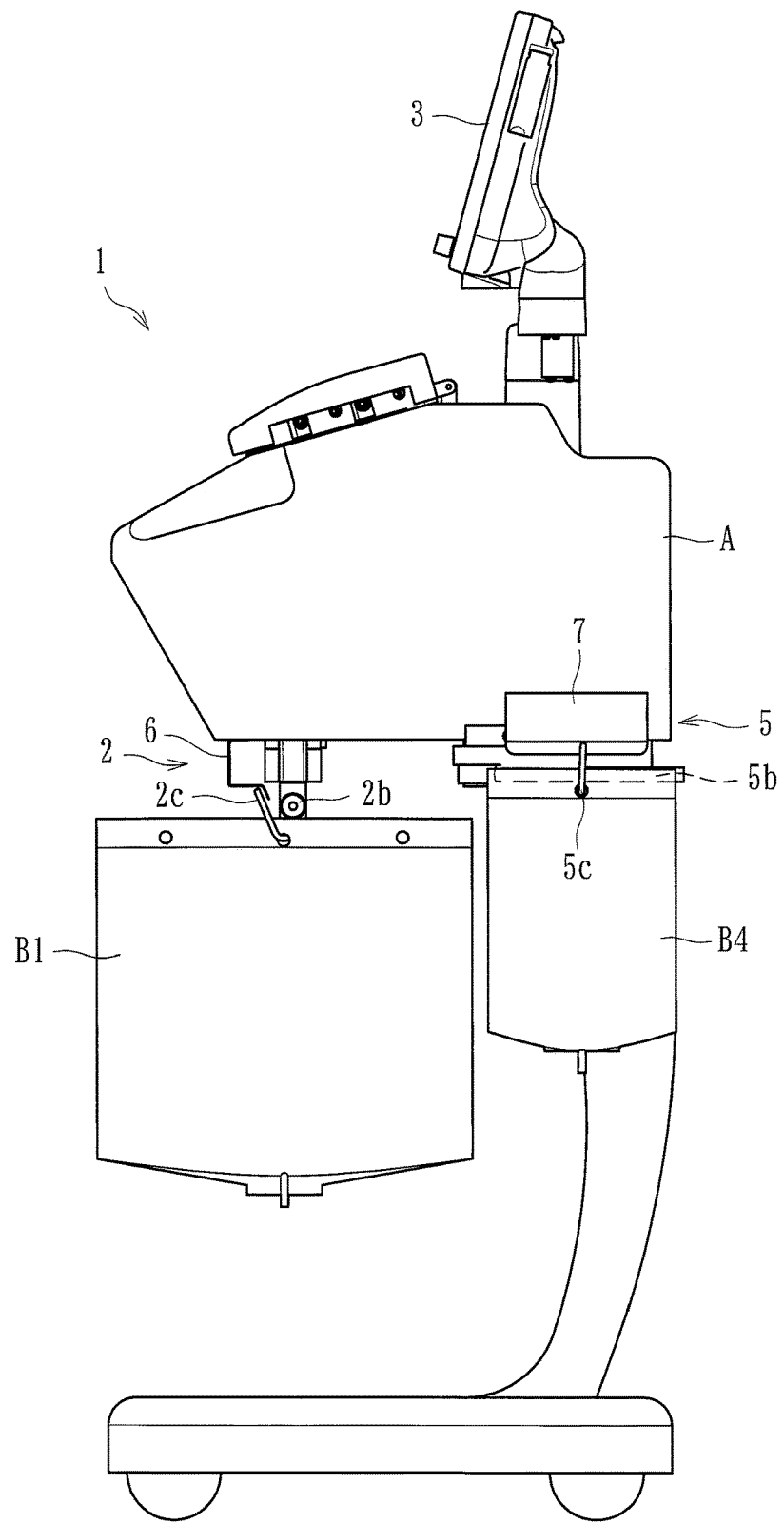

[Fig 5]
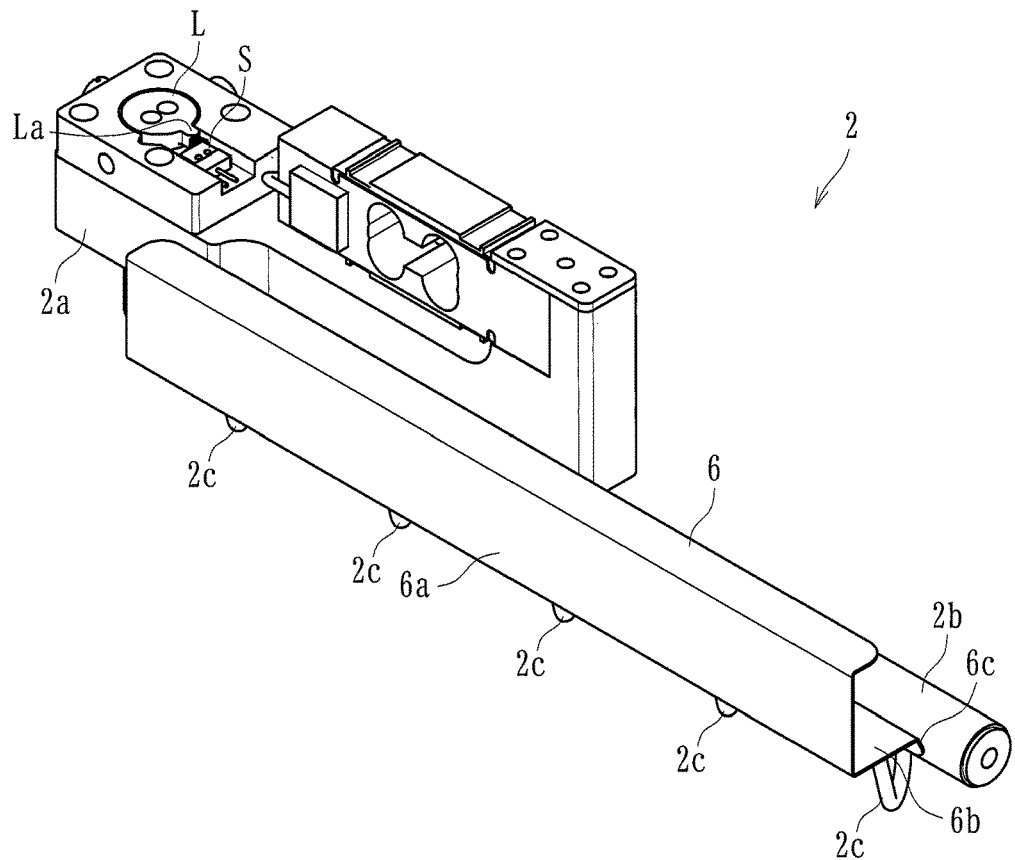
[Fig 6]
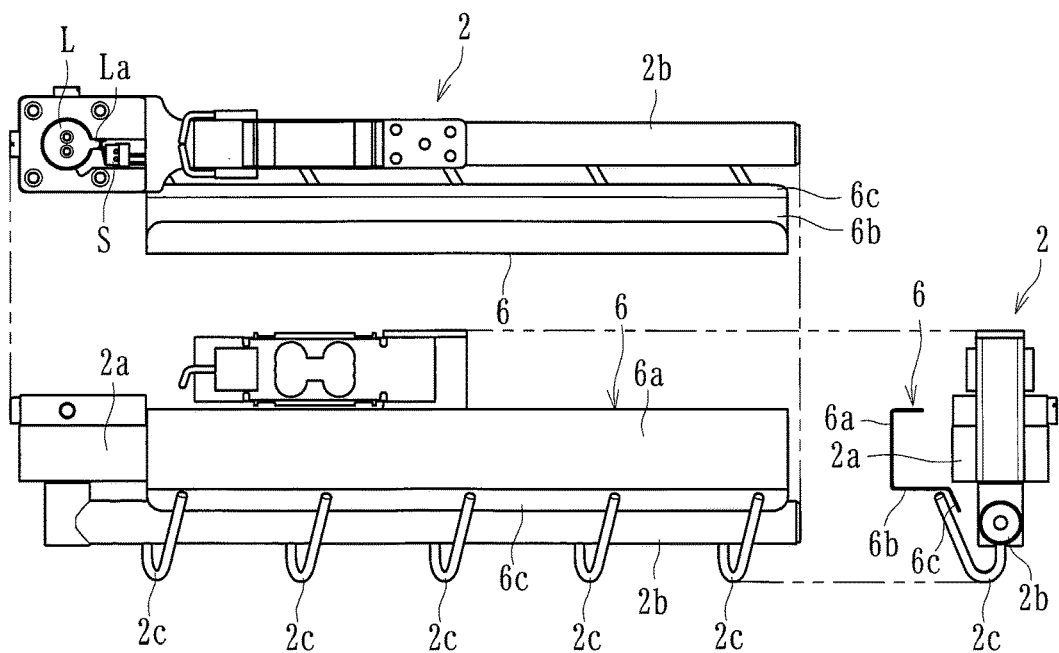

[Fig 7]
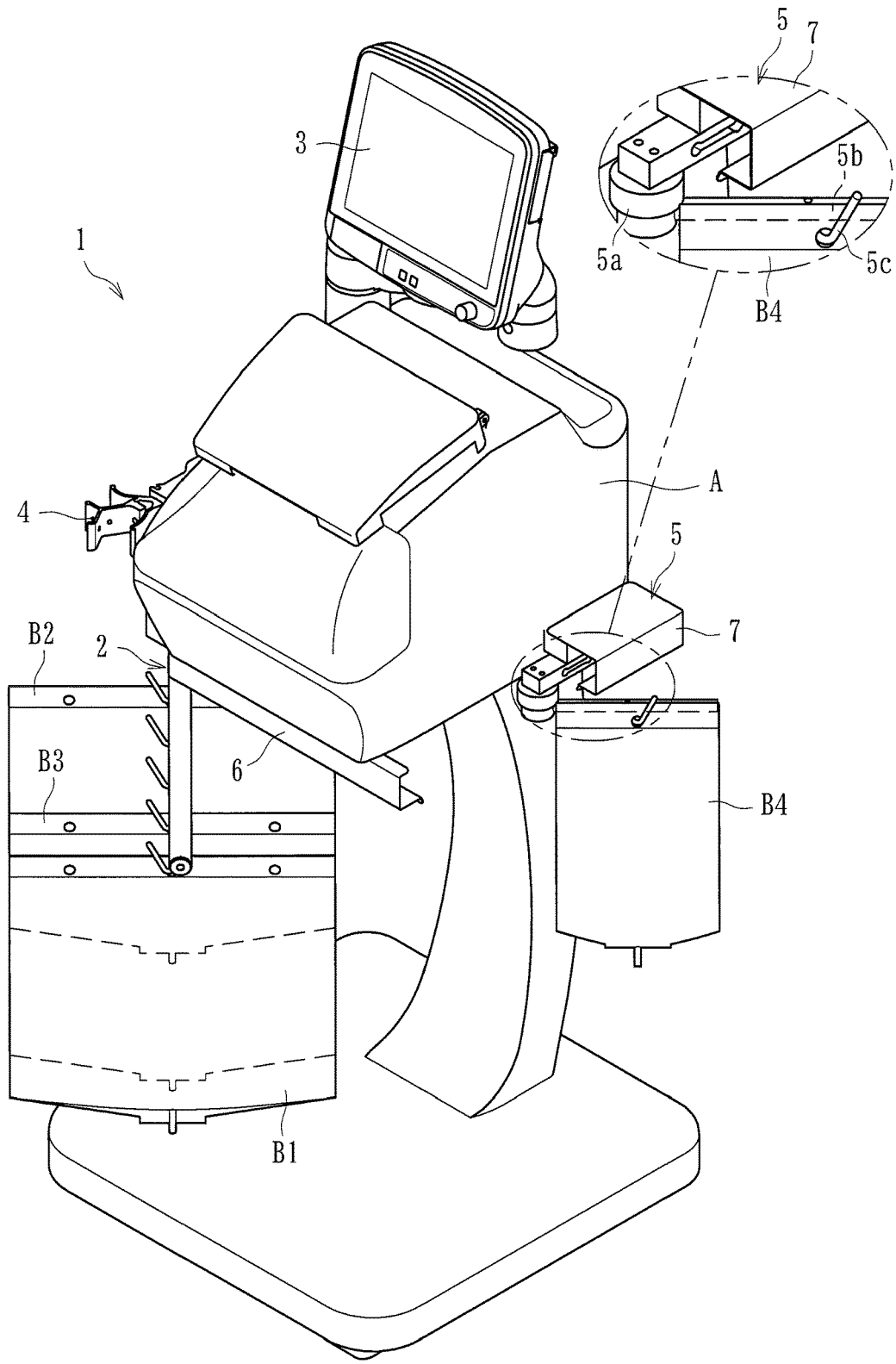

[Fig 8]
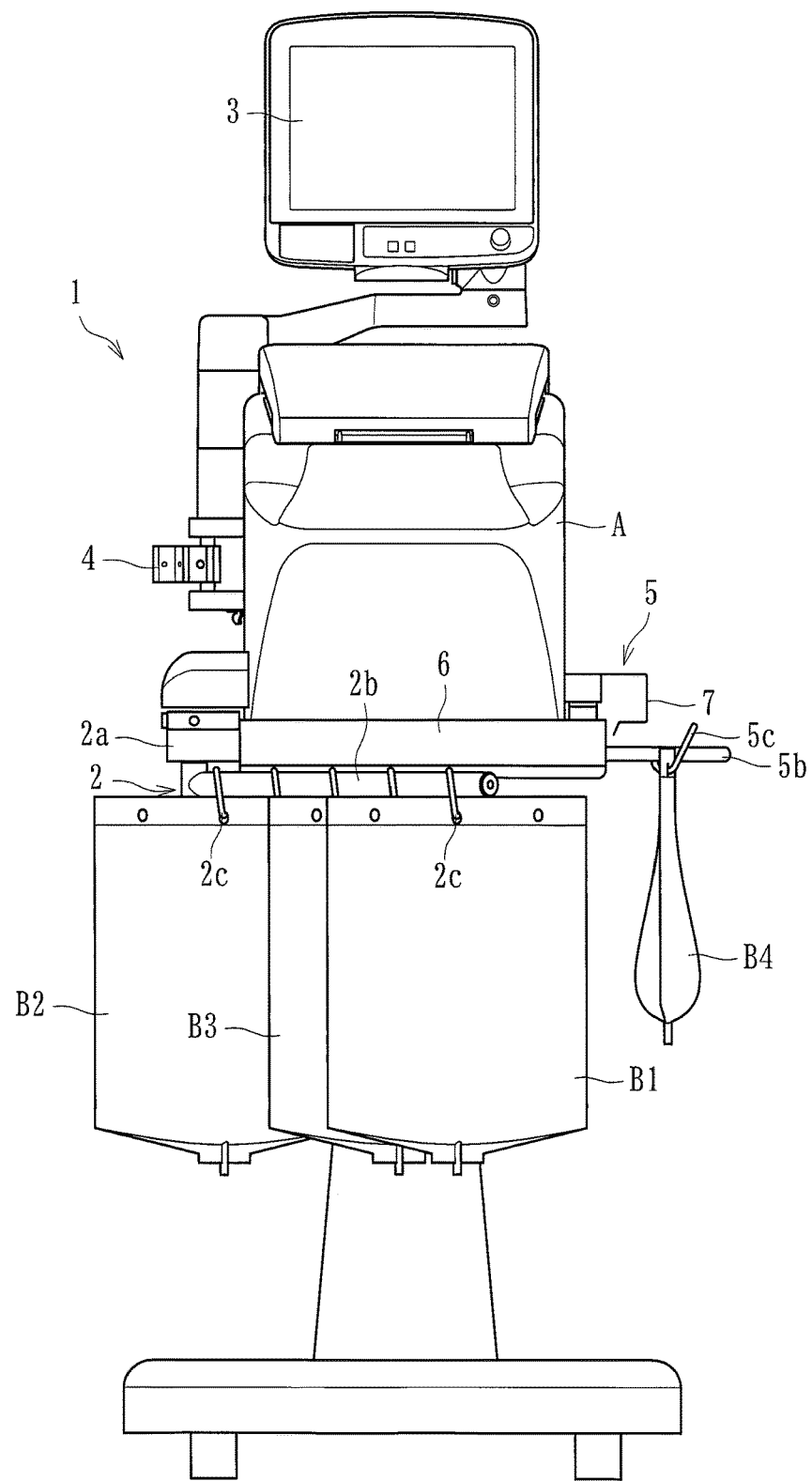

[Fig 9]
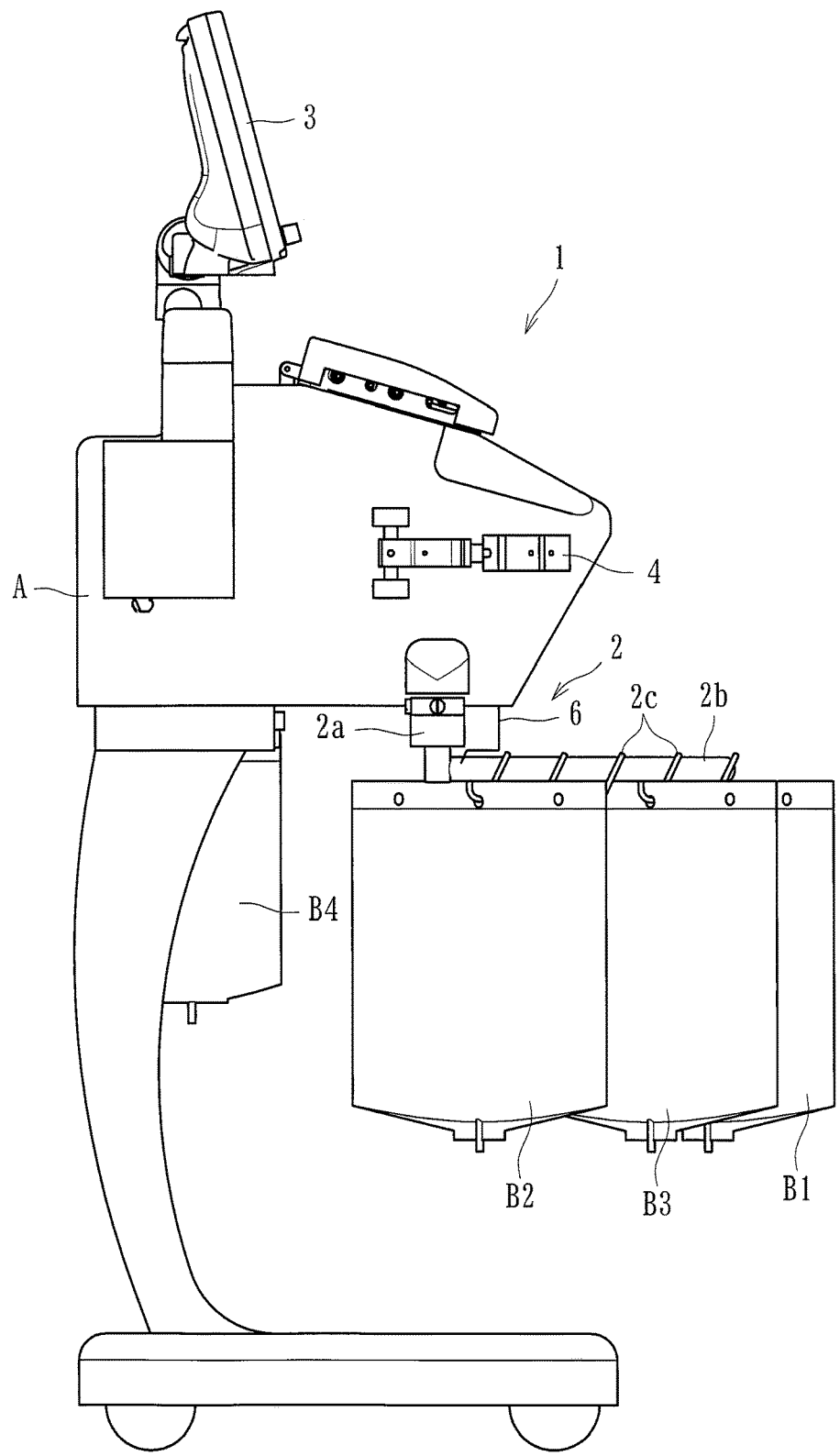

[Fig 10]
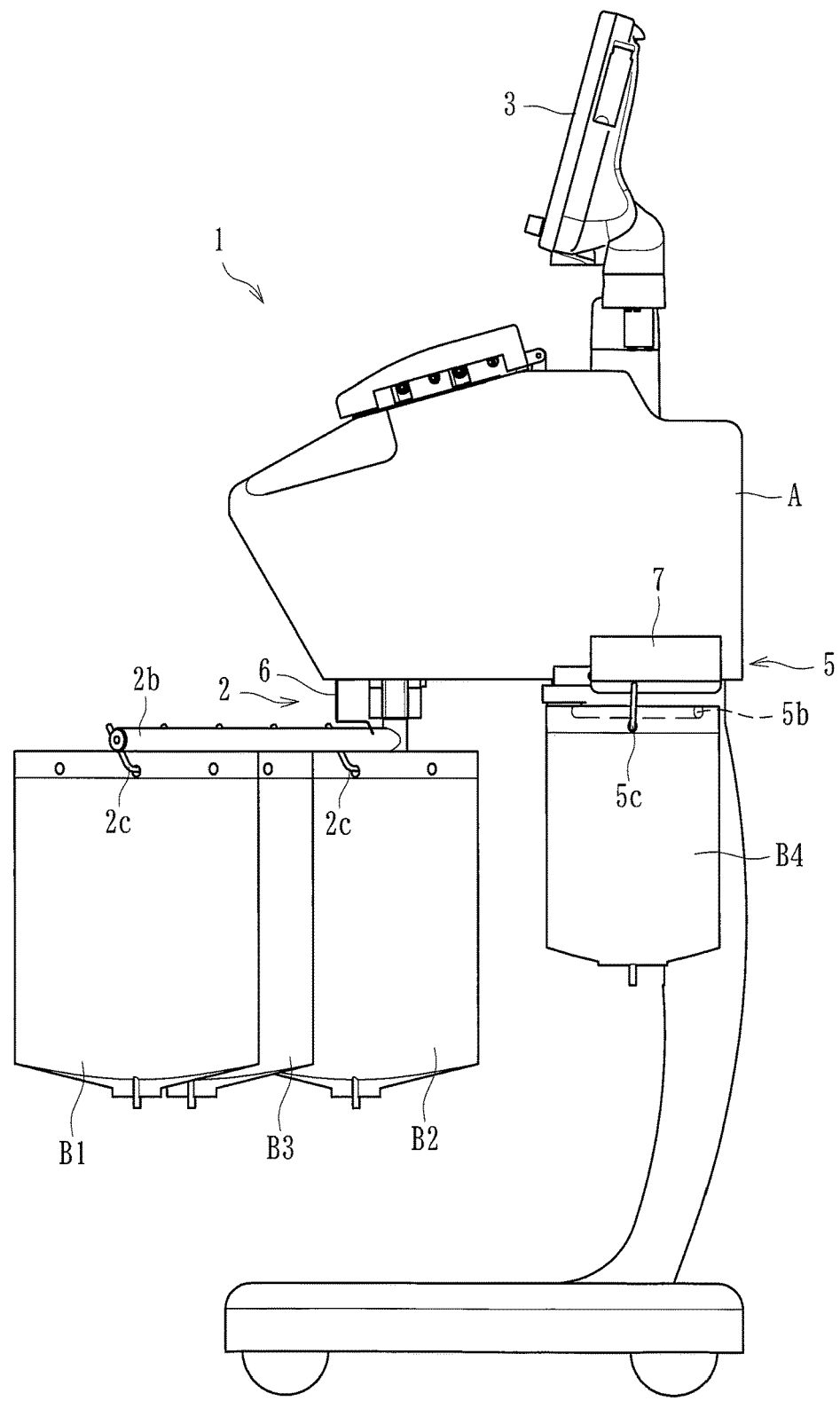

[ Fig 11 ]
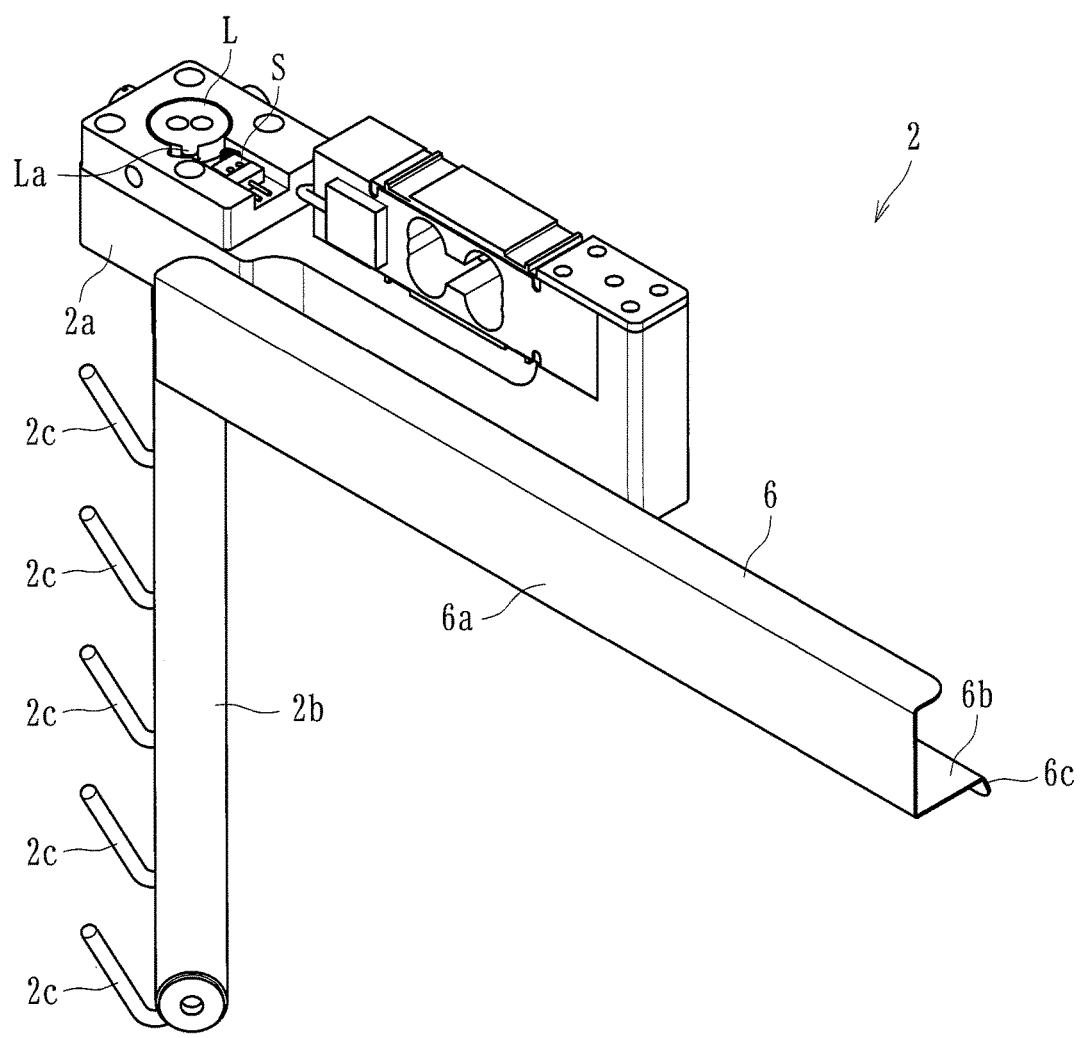

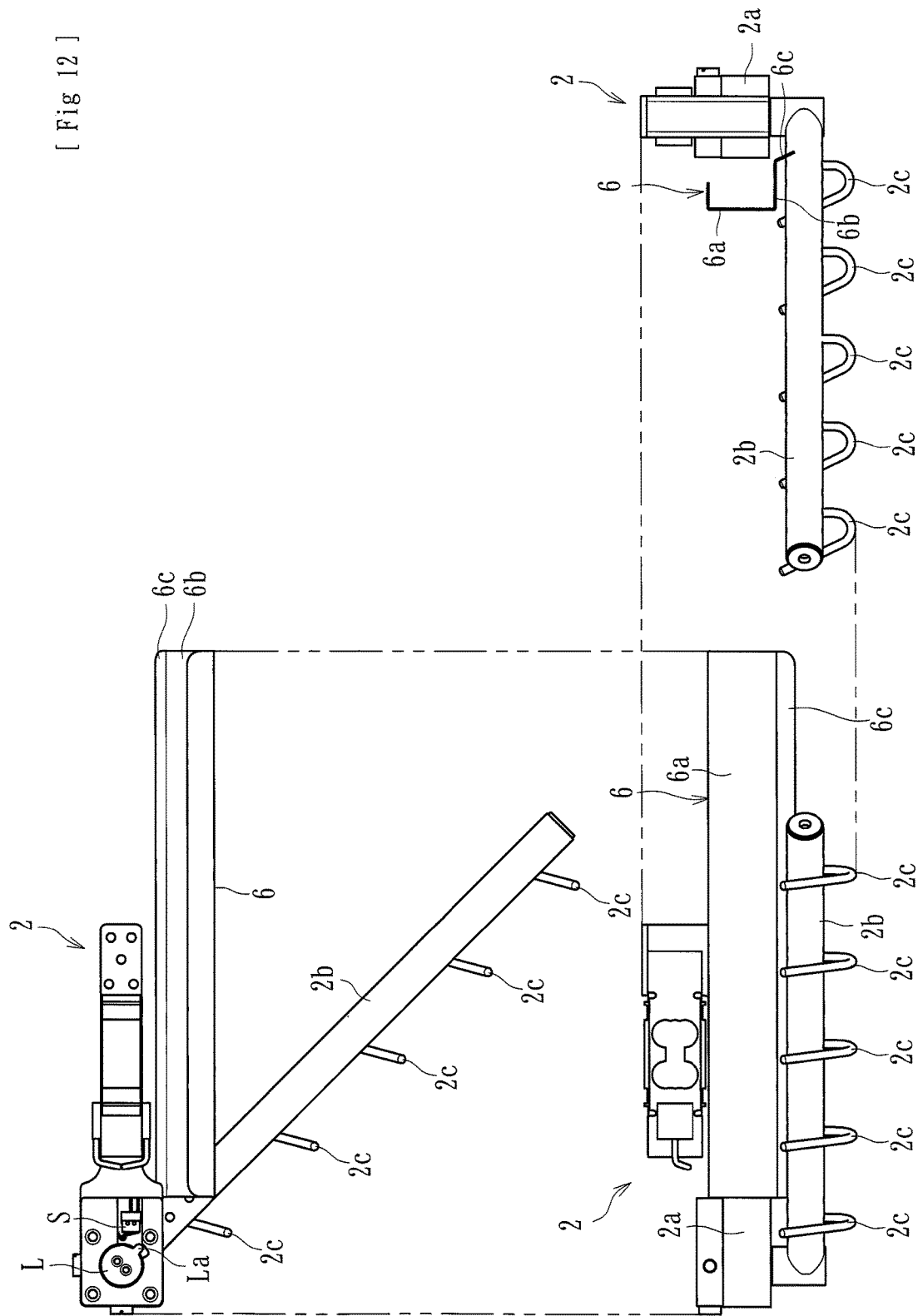

[Fig 13]
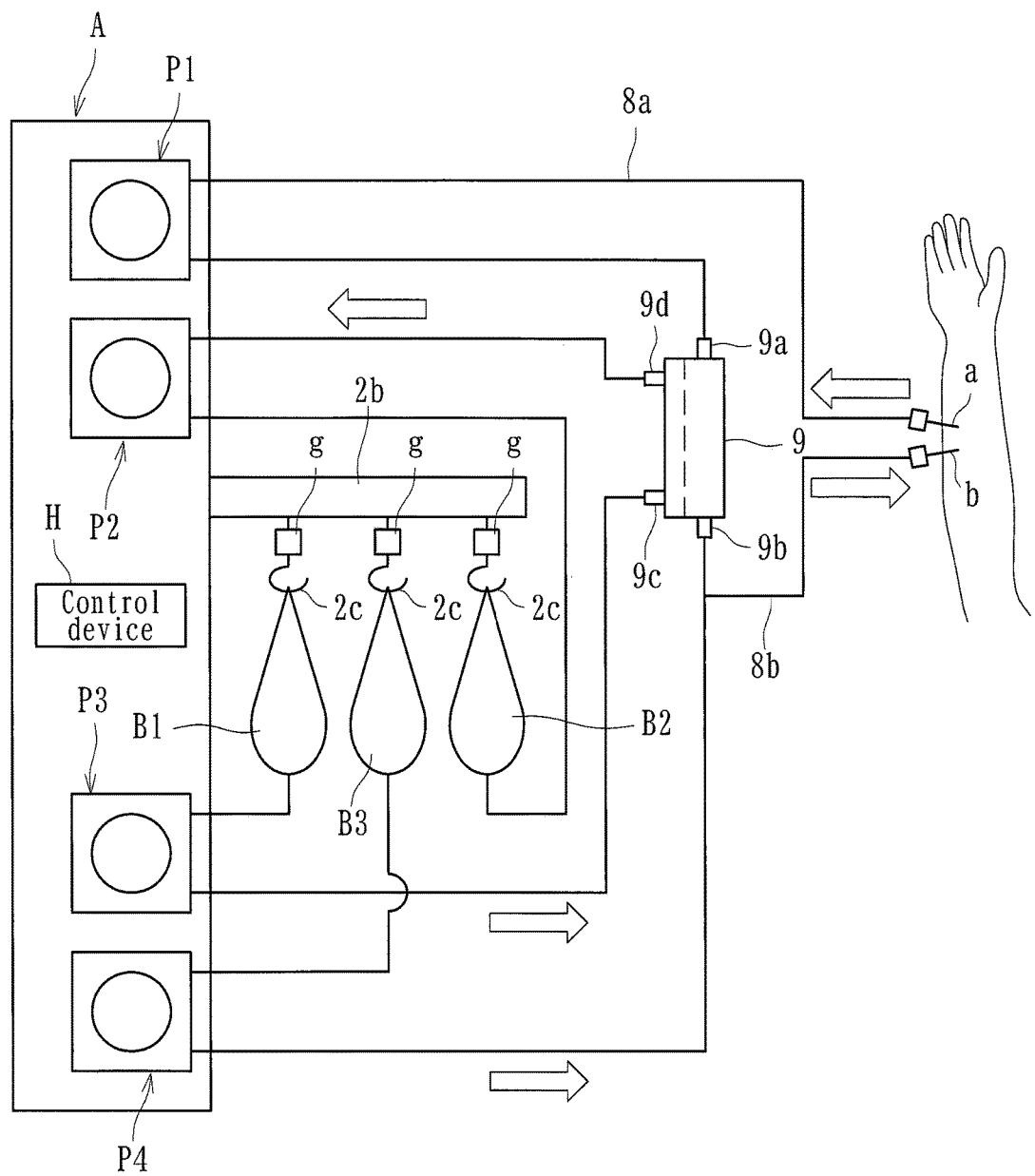

[Fig 14]
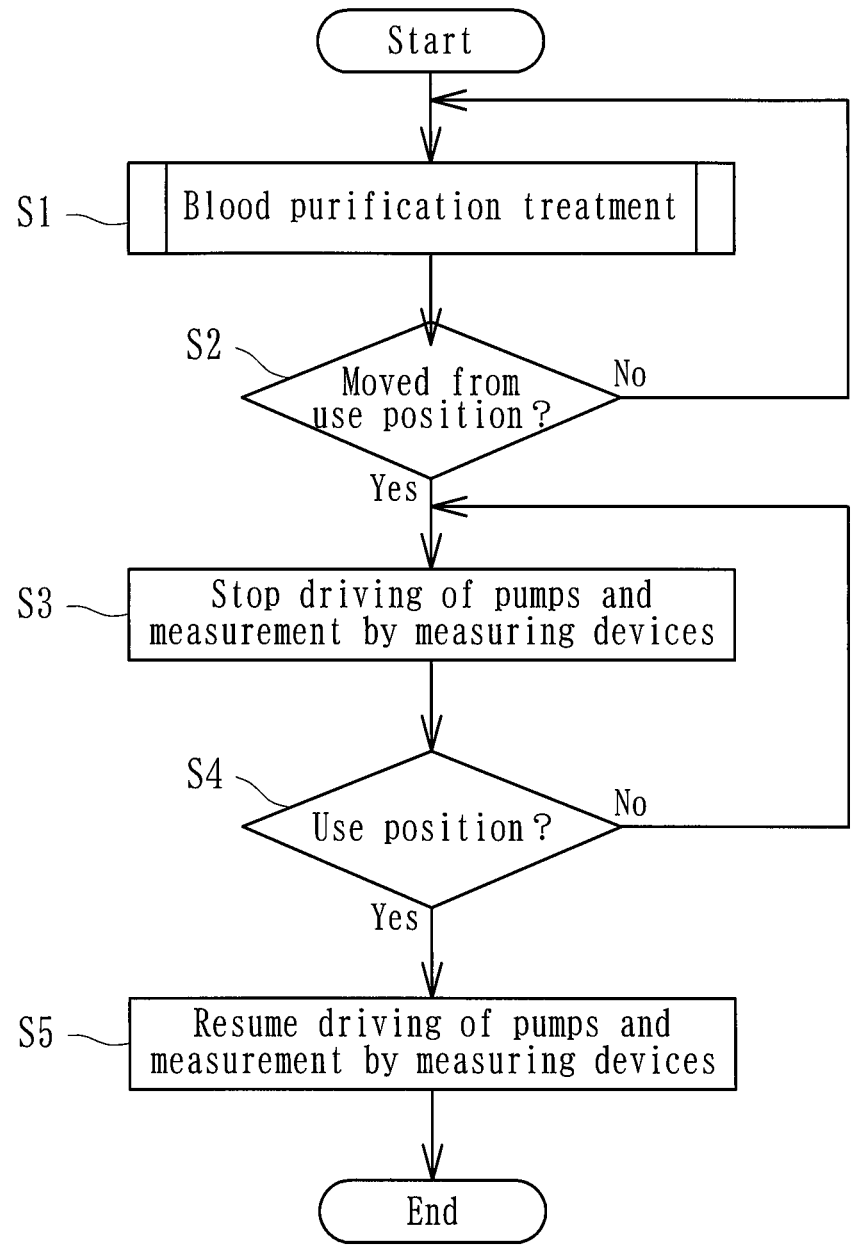

[Fig 15]
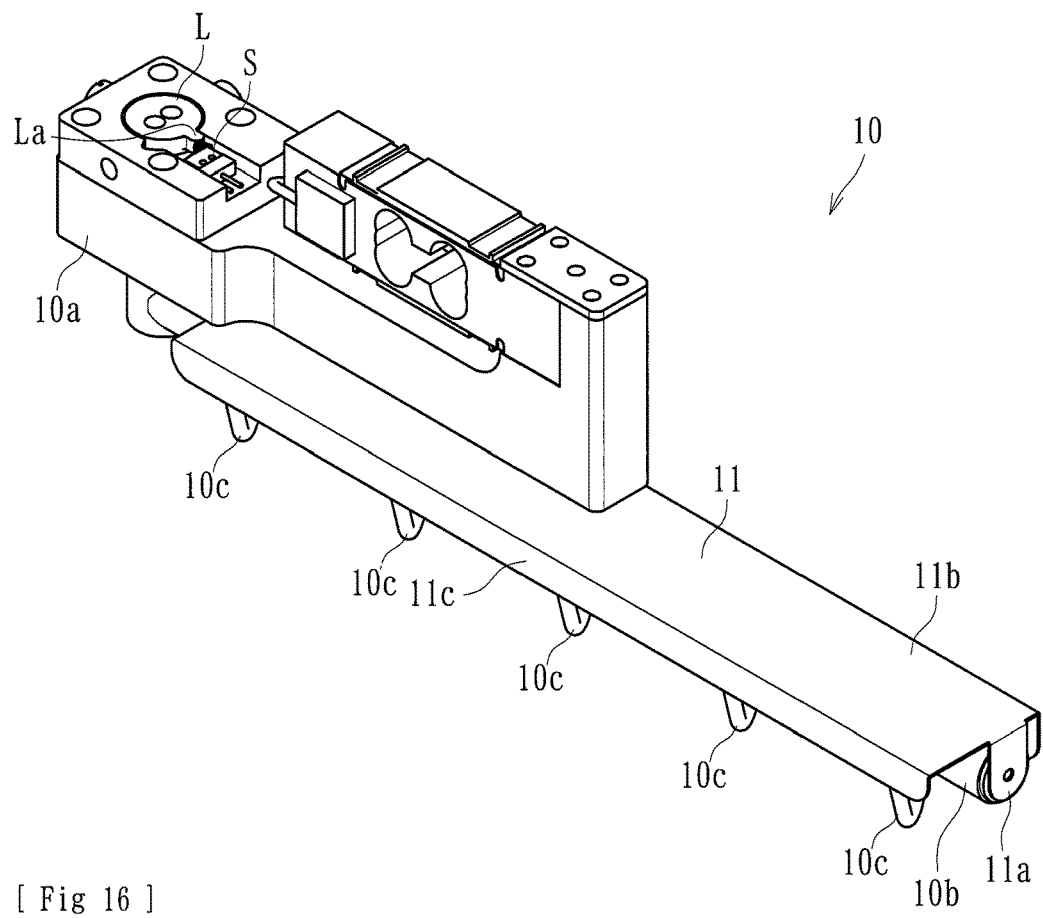
[Fig 16]
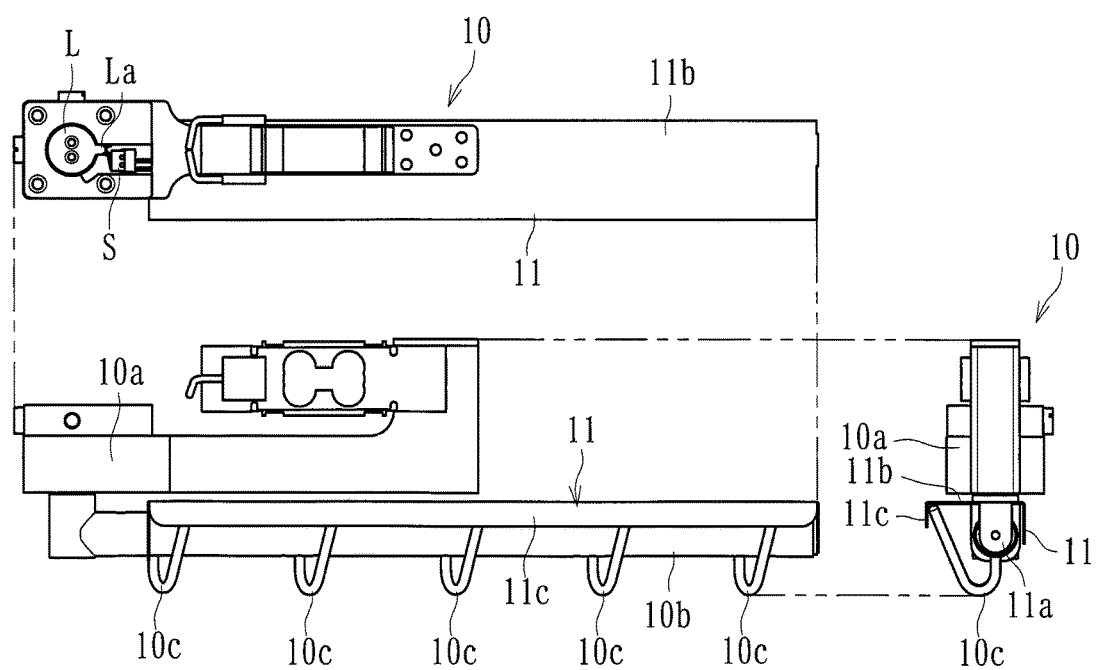

[Fig 17]
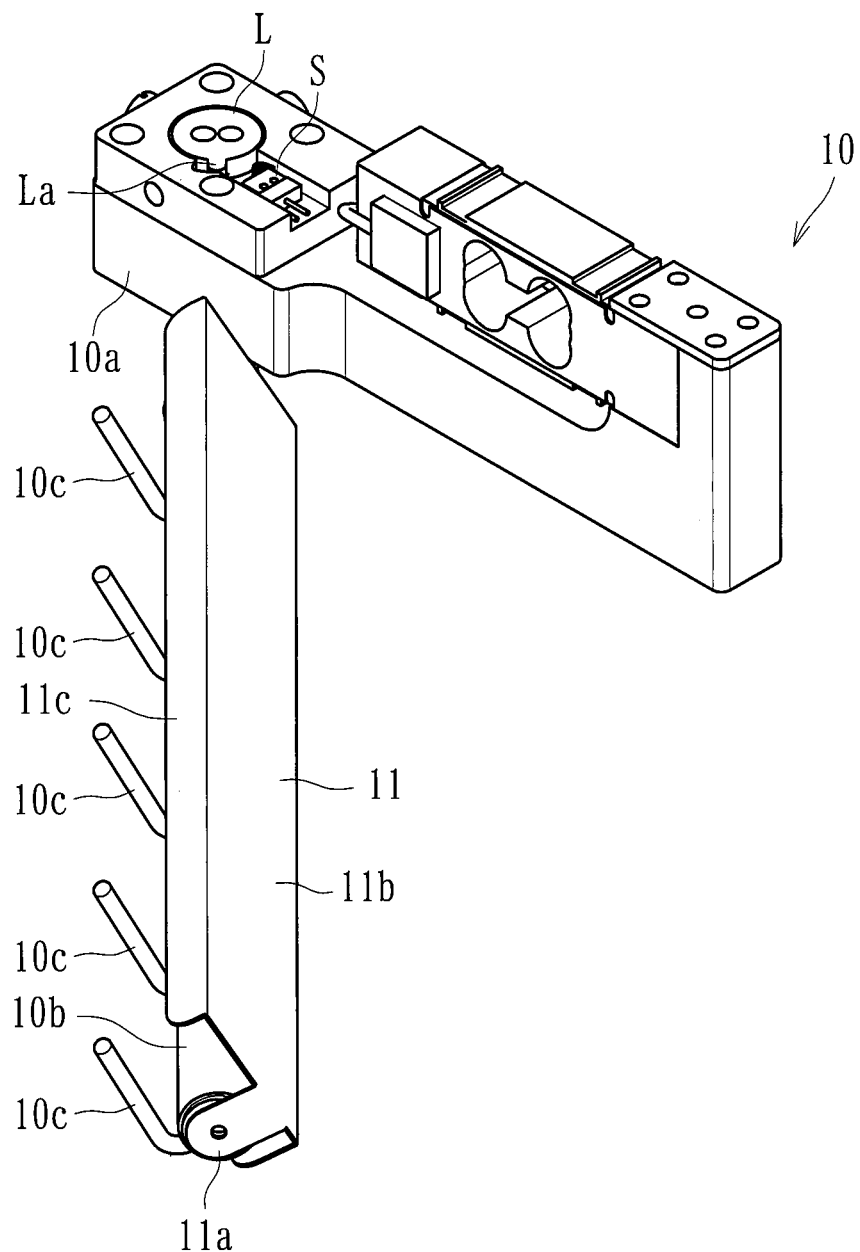

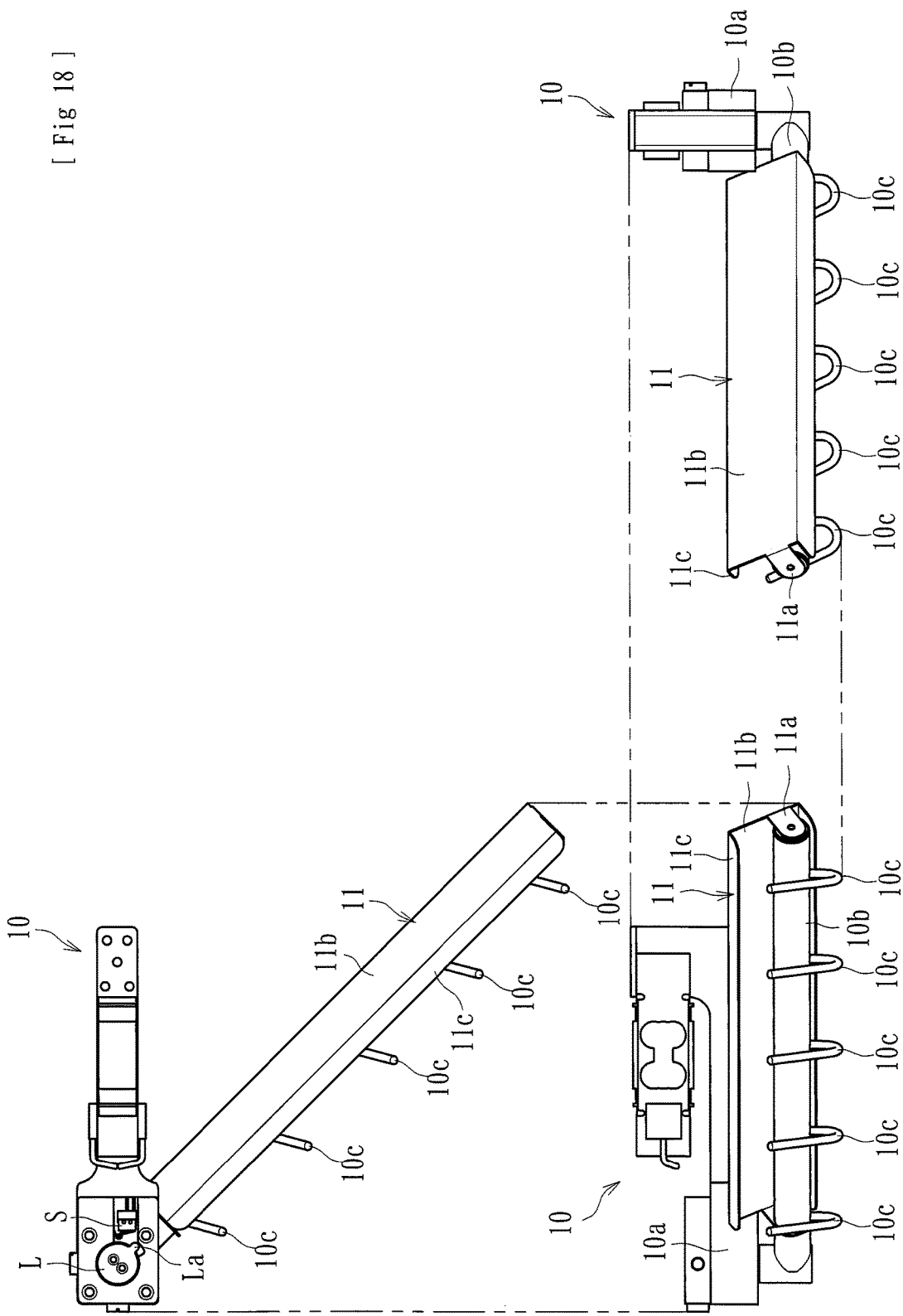
[Fig 18]

[Fig 19]
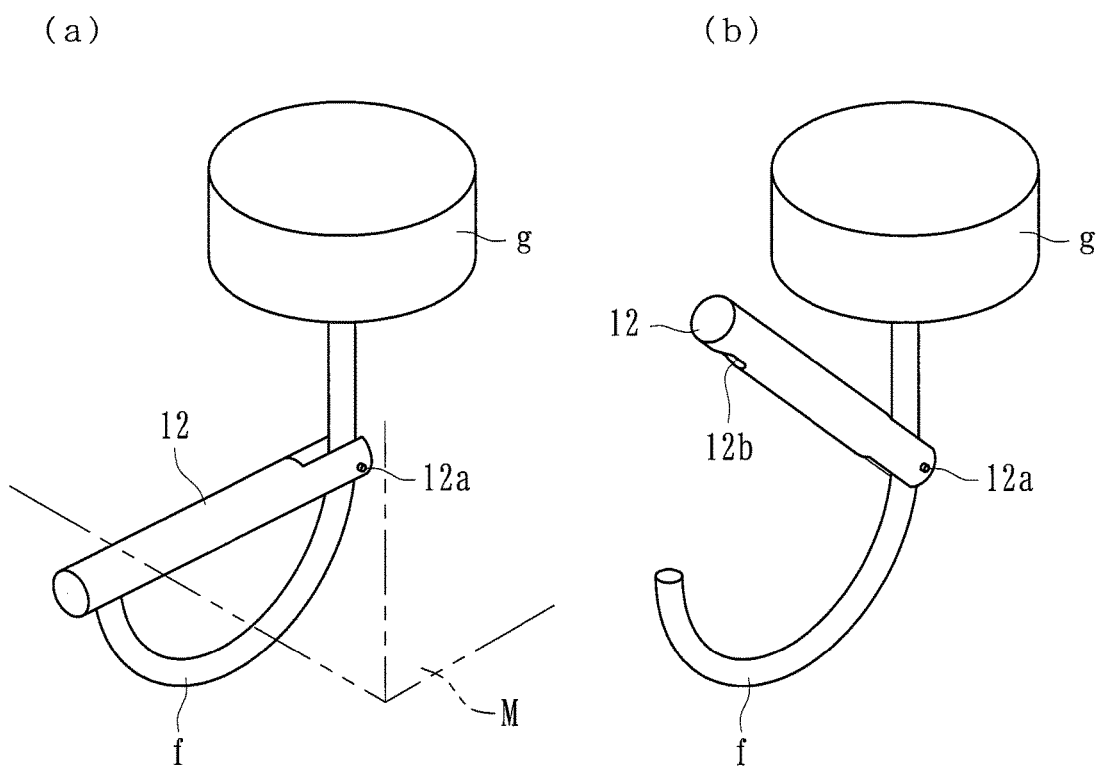

BLOOD PURIFICATION APPARATUS

FIELD

The present invention relates to a blood purification apparatus that includes a holding device capable of holding a container bag containing a liquid for blood purification treatment, such as dialysate, substitution fluid, or anticoagulant, and that is capable of performing blood purification treatment using the liquid in the container bag.

BACKGROUND

A conventional blood purification apparatus that performs blood purification treatment using container bags in which dialysate, substitution fluid, and the like are contained (a dialysate bag and a substitution fluid bag) includes a hanger portion having hook portions to which the container bags can be attached, and a measuring device (load meter) capable of measuring the weights of the container bags held by the hanger portion. For example, by a peristaltic pump, dialysate is supplied from a container bag in which dialysate is contained (container bag for dialysate) to a blood purifier (dialyzer) at a predetermined flow rate, and drainage from the blood purifier is caused to be contained in another container bag (container bag for drainage) at a predetermined flow rate. For example, by another peristaltic pump, substitution fluid can also be supplied from a container bag in which substitution fluid is contained (container bag for substitution fluid) to a blood circuit at a predetermined flow rate.

In the above conventional blood purification apparatus, when in the middle of blood purification treatment, the dialysate in the container bag for dialysate or the substitution fluid in the container bag for substitution fluid is consumed and the container bag becomes empty, or the container bag for drainage is filled with drainage, the container bag needs to be appropriately replaced by a worker. When replacing the container bag, by the operation of the worker, the control relating to the blood purification treatment such as supply of dialysate and substitution fluid, the measurement by the measuring device, and the like are temporarily stopped, and the desired container bag is replaced in the temporarily stopped state, and then the control relating to the blood purification treatment is resumed. Because such a prior art is not related to inventions publicly known through literature, there is no information on prior art literature to be described.

SUMMARY

However, in the above conventional art, there is a possibility that a container bag is replaced without stopping the control relating to the blood purification treatment, the measurement by the measuring device, and the like, or a worker erroneously detaches or adds a container bag. There is a problem in that, because, in that case, the weight of the container bag measured by the measuring device changes suddenly, the weight measured by the measuring device may be determined to be abnormal and an alarm may be raised, and therefore a wasteful work for turning off such a false alarm is needed.

If, during the blood purification treatment, for example, a container bag held by the hanger portion is damaged and the liquid contained therein flows out to the outside, the weight of the container bag measured by the measuring device decreases suddenly. There is also a problem in that, in that case, the blood purification apparatus cannot distinguish between a weight decrease due to damage to the container bag and a weight decrease due to the fact that a worker detached the container bag from the hanger portion.

The present invention has been made in consideration of such circumstances, and an object of the present invention is to provide a blood purification apparatus in which inadvertent replacement of a container bag attached to a hanger portion can be avoided.

According to the present teachings, there is provided a blood purification apparatus including a holding device capable of holding a container bag that contains a liquid for blood purification treatment, such as dialysate, substitution fluid, or anticoagulant, the blood purification apparatus being capable of performing blood purification treatment using the liquid in the container bag, wherein the holding device includes a hanger portion including an attachment portion to which the container bag can be attached, and movable between a use position in which the container bag is used and a replacement position in which the container bag is replaced, a measuring device capable of measuring the weight of the container bag held by the hanger portion, and a restricting device that restricts attachment and detachment of the container bag to and from the attachment portion when the hanger portion is in the use position.

According to the present teachings, there is provided the blood purification apparatus according to the teachings herein, wherein the restricting device is a shielding plate that is fixed to an apparatus main body and that covers and shields the attachment portion only when the hanger portion is in the use position.

According to the present teachings, there is provided the blood purification apparatus according to the teachings herein, wherein the restricting device is a shielding plate that is attached to the hanger portion and that is movable between a first position in which the attachment portion is shielded and a second position in which the attachment portion is open, the restricting device being movable from the first position to the second position only when the hanger portion is in the replacement position.

According to the present teachings, there is provided the blood purification apparatus according to the teachings herein, further comprising a detecting device detecting that the hanger portion is in the use position, and wherein when, during the blood purification treatment, the detecting device does not detect that the hanger portion is in the use position, it is informed that the hanger portion is not in the use position.

According to the present teachings, there is provided the blood purification apparatus according to the teachings herein, further comprising a detecting device detecting that the hanger portion is in the use position, and wherein when, during the blood purification treatment, the detecting device does not detect that the hanger portion is in the use position, control relating to the blood purification treatment is stopped.

According to the present teachings, there is provided the blood purification apparatus according to the teachings herein, wherein when, after the control relating to the blood purification treatment is stopped, the detecting device detects that the hanger portion is in the use position, the control relating to the blood purification treatment is resumed.

According to the present teachings, the holding device includes a restricting device that restricts attachment and detachment of the container bags to and from the attachment portion when the hanger portion is in the use position.

Therefore, inadvertent replacement of the container bags attached to the hanger portion can be avoided.

According to the present teachings, the restricting device is a shielding plate that is fixed to an apparatus main body and that covers and shields the attachment portion only when the hanger portion is in the use position. Therefore, inadvertent replacement of the container bag when the hanger portion is in the use position can be reliably avoided, and the configuration of the hanger portion can be simplified.

According to the present teachings, the restricting device is a shielding plate that is attached to the hanger portion and that is movable between a first position in which the attachment portion is shielded and a second position in which the attachment portion is open, the restricting device being movable from the first position to the second position only when the hanger portion is in the replacement position. Therefore, inadvertent replacement of the container bag when the hanger portion is in the use position can be reliably avoided, and the restricting device can be caused to follow the hanger portion.

According to the present teachings, the blood purification apparatus further includes a detecting device detecting that the hanger portion is in the use position, and when, during the blood purification treatment, the detecting device does not detect that the hanger portion is in the use position, it is informed that the hanger portion is not in the use position. Therefore, the worker can reliably grasp that the hanger portion is not in a position in which the container bag can be replaced.

According to the present teachings, the blood purification apparatus further includes a detecting device detecting that the hanger portion is in the use position, and when, during the blood purification treatment, the detecting device does not detect that the hanger portion is in the use position, control relating to the blood purification treatment is stopped. Therefore, inadvertent replacement of the container bag during the blood purification treatment can be reliably avoided.

According to the present teachings, when, after the control relating to the blood purification treatment is stopped, the detecting device detects that the hanger portion is in the use position, the control relating to the blood purification treatment is resumed. Therefore, the control relating to the blood purification treatment is performed only when the hanger portion is in the use position (that is, when the replacement of the container bag is restricted by the restricting device), and inadvertent replacement of the container bag during the blood purification treatment can be reliably avoided, and the resumption after the stop of the control relating to the blood purification treatment can be performed automatically.

BRIEF DESCRIPTION OF THE DRAWINGS

FIG. 1 is a perspective view showing a blood purification apparatus according to a first embodiment of the present invention (with a hanger portion in the use position).

FIG. 2 is a front view showing the blood purification apparatus.

FIG. 3 is a left side view showing the blood purification apparatus.

FIG. 4 is a right side view showing the blood purification apparatus.

FIG. 5 is a perspective view showing a holding device of the blood purification apparatus (with the hanger portion in the use position).

FIG. 6 includes three views showing the holding device (with the hanger portion in the use position).

FIG. 7 is a perspective view showing the blood purification apparatus (with the hanger portion in the replacement position).

FIG. 8 is a front view showing the blood purification apparatus (with the hanger portion in the replacement position).

FIG. 9 is a left side view showing the blood purification apparatus (with the hanger portion in the replacement position).

FIG. 10 is a right side view showing the blood purification apparatus (with the hanger portion in the replacement position).

FIG. 11 is a perspective view showing the holding device in the blood purification apparatus (with the hanger portion in the replacement position).

FIG. 12 includes three views showing the holding device (with the hanger portion in the replacement position).

FIG. 13 is a schematic view showing the blood purification apparatus.

FIG. 14 is a flowchart showing the content of the control of the blood purification apparatus.

FIG. 15 is a perspective view showing a holding device of a blood purification apparatus according to a second embodiment of the present invention (with a hanger portion in the use position).

FIG. 16 includes three views showing the holding device (with the hanger portion in the use position).

FIG. 17 is a perspective view showing the holding device of the blood purification apparatus (with the hanger portion in the replacement position).

FIG. 18 includes three views showing the holding device (with the hanger portion in the replacement position).

FIG. 19 includes perspective views showing a restricting device in a blood purification apparatus according to another embodiment of the present invention. (a) is a schematic diagram showing a state where a hanger portion is in the use position. (b) is a schematic diagram showing a state where the hanger portion is in the replacement position.

DETAILED DESCRIPTION

Embodiments of the present teachings will be described below specifically with reference to the drawings.

A blood purification apparatus 1 according to a first embodiment is for providing a patient with blood purification treatment (treatment such as hemodialysis (HD), hemodiafiltration (HDF), hemofiltration (HF), or continuous hemodiafiltration (CHF)), and, as shown in FIGS. 1 to 13, includes an apparatus main body A in which a holding device 2 holding container bags B1 to B3, a display 3, a clamping device 4, a holding device 5 holding a container bag B4, a control device H, and peristaltic pumps (P1 to P4) are formed.

The container bags B1 to B4 are bag-like containers made of nylon or the like for containing liquid for the blood purification treatment. For example, the container bag B1 contains dialysate to be supplied to a dialyzer 9 (see FIG. 13), the container bag B2 contains drainage from the dialyzer 9, the container bag B3 contains substitution fluid, and the container bag B4 contains a drug administered during the blood purification treatment, such as anticoagulant.

The display 3 is, for example, a touch panel having a liquid crystal screen or the like, and is configured to be capable of displaying the setting relating to the blood purification treatment, the state of a patient, and the like. The clamping device 4 is capable of clamping the dialyzer 9, and is configured such that the blood of the patient can be purified by the dialyzer 9. The dialyzer 9 is formed by housing a plurality of hollow fibers with pores in a case, in which a blood inlet port 9a, a blood outlet port 9b, a dialysate inlet port 9c, and a dialysate outlet port 9d are formed.

The proximal end of an arterial blood circuit 8a is connected to the blood inlet port 9a, and the proximal end of a venous blood circuit 8b is connected to the blood outlet port 9b. A blood pump, which is a peristaltic pump P1, is disposed in the middle of the arterial blood circuit 8a. An arterial puncture needle (a) and a venous puncture needle (b) that can be inserted into the patient can be attached to the distal ends of the arterial blood circuit 8a and the venous blood circuit 8b, respectively. When, after the arterial puncture needle (a) and the venous puncture needle (b) are inserted into the patient, the peristaltic pump P1 is driven, the blood of the patient can be circulated extracorporeally through the arterial blood circuit 8a and the venous blood circuit 8b, and blood purification by the dialyzer 9 is performed in the process of the extracorporeal circulation.

The dialysate inlet port 9c is connected through the peristaltic pump P3 to the container bag B1. By driving the peristaltic pump P3 (dialysate pump), the dialysate in the container bag B1 can be supplied to the dialyzer 9. The dialysate outlet port 9d is connected through the peristaltic pump P2 to the container bag B2. By driving the peristaltic pump P2 (dialysate pump), drainage from the dialyzer 9 can be contained in the container bag B2. The container bag B3 is connected through a substitution pump, which is a peristaltic pump P4, to the venous blood circuit 8b. By driving the peristaltic pump P4, the substitution fluid in the container bag B3 can be supplied to the venous blood circuit 8b.

The holding device 2 is for holding the above-described container bags, and includes a main body portion 2a, a hanger portion 2b that has attachment portions 2c to which the container bags (B1 to B3) can be attached, and that is movable between a use position in which the container bags (B1 to B3) are used (see FIGS. 1 to 6) and a replacement position in which the container bags (B1 to B3) are replaced (see FIGS. 7 to 12), and measuring devices (g) capable of measuring the weights of the container bags (B1 to B3) held by the hanger portion 2b (see FIG. 13).

The main body portion 2a movably supports the hanger portion 2b, and includes, in this embodiment, a shaft portion L for swinging the hanger portion 2b, and a detecting device S, which is a sensor capable of detecting that the shaft portion L is in a predetermined position. That is, when the hanger portion 2b is under the main body portion 2a as shown in FIGS. 5 and 6, the hanger portion 2b is in the "use position." When the hanger portion 2b is swung about the shaft portion L, and the hanger portion 2b is in a position distant from the main body portion 2a as shown in FIGS. 11 and 12, the hanger portion 2b is in the "replacement position."

The shaft portion L is a rotating shaft that rotates with the swing of the hanger portion 2b, and a protrusion La is formed on part thereof. When the hanger portion 2b is in the use position, the protrusion La is detected by the detecting device S, and an electric signal is transmitted to the control device H. That is, it can be detected that the hanger portion 2b is in the use position, from the fact that the detecting device S is in an ON state (it can also be detected that the hanger portion 2b is not in the use position, from the fact that the detecting device S is in an OFF state).

The hanger portion 2b is a bar-like member one end of which is attached to the shaft portion L, and has attachment portions 2c formed at predetermined intervals. The attachment portions 2c are hooks from which the container bags (B1 to B3) can be hung and that can hold them, and the measuring devices (g) are disposed at the respective proximal ends thereof. The measuring devices (g) are load meters that measure applied loads, and measure the weights of the container bags (B1 to B3) hung from the attachment portions 2c (the total weights of the container bags and the contents), and can transmit the measured values as electric signals to the control device H.

By measuring the weights of the container bags B1 and B2 with the measuring devices g and controlling the driving of the peristaltic pumps P2 and P3 according to the weights, dialysate can be supplied to the dialyzer 9 at a predetermined flow rate, and drainage can be discharged from the dialyzer 9 at a predetermined flow rate. By measuring the weight of the container bag B3 with the measuring device g and controlling the driving of the peristaltic pump P4 according to the weight, substitution fluid can be supplied to the venous blood circuit 8b at a predetermined flow rate.

The holding device 2 according to this embodiment has a restricting device 6 that restricts the attachment and detachment of the container bags (B1 to B3) to and from the attachment portions 2c when the hanger portion 2b is in the use position. The restricting device 6 is a shielding plate that is fixed to the apparatus main body A and that covers and shields the attachment portions 2c only when the hanger portion 2b is in the use position, and is formed, for example, by pressing a metal plate material into a substantially U shape, so as to have a front portion 6a, a lower surface portion 6b, and a flange portion 6c.

That is, when the hanger portion 2b is in the use position, as shown in FIGS. 5 and 6, the front portion 6a, the lower surface portion 6b, and the flange portion 6c of the restricting device 6 cover and shield the attachment portions 2c formed in the hanger portion 2b and restrict the attachment and detachment of the container bags (B1 to B3) to and from the attachment portions 2c (physically restrict the attachment and detachment). When the hanger portion 2b is swung from the use position to the replacement position, as shown in FIGS. 11 and 12, the hanger portion 2b is distant from the restricting device 6 and the attachment portions 2c are not shielded, and the attachment and detachment of the container bags (B1 to B3) to and from the attachment portions 2c are allowed.

In this embodiment, when, during the blood purification treatment, the detecting device S does not detect that the hanger portion 2b is in the use position (that is, when the hanger portion 2b is not in the use position), it is informed that the hanger portion 2b is not in the use position. Such information may be displayed by the display 3, or may be output by a speaker, a warning light, or the like (not shown). The worker can thereby reliably grasp that the hanger portion 2b is not in a position in which the container bags (B1 to B3) can be replaced (replacement position).

The control device H according to this embodiment is configured to stop the control relating to the blood purification treatment when, during the blood purification treatment, the detecting device S does not detect that the hanger portion 2b is in the use position, and to resume the control relating to the blood purification treatment when, after the control relating to the blood purification treatment is stopped, the detecting device S detects that the hanger portion 2b is in the use position.

Since, as described above, the control relating to the blood purification treatment is stopped when, during the blood purification treatment, the detecting device S does not detect that the hanger portion 2b is in the use position, inadvertent replacement of the container bags (B1 to B3) during the blood purification treatment can be reliably avoided. Since the control relating to the blood purification treatment is resumed when, after the control relating to the blood purification treatment is stopped, the detecting device S detects that the hanger portion 2b is in the use position, the control relating to the blood purification treatment is performed only when the hanger portion 2b is in the use position (that is, when the replacement of the container bags (B1 to B3) is restricted by the restricting device 6), and inadvertent replacement of the container bags (B1 to B3) during the blood purification treatment can be reliably avoided, and the resumption after the stop of the control relating to the blood purification treatment can be performed automatically.

In this embodiment, the container bag B4 containing a drug administered during the blood purification treatment, such as anticoagulant, is held by the holding device 5. As with the holding device 2, the holding device 5 has a hanger portion 5b in which an attachment portion 5c, which is a hook, is formed. A restricting device 7 that restricts the attachment and detachment of the container bag B4 to and from the attachment portion 5c when the hanger portion is in the use position as shown in FIG. 2 is attached to the apparatus main body A.

Next, the content of the control by the control device H according to this embodiment will be described with reference to the flowchart of FIG. 14.

First, the hanger portion 2b is set in the replacement position, the container bags (B1 to B3) are attached to the attachment portions 2c of the holding device 2, the container bag B4 is attached to the attachment portion 5c of the holding device 5, and then the hanger portion 2b (the same goes for the hanger portion 5b of the holding device 5) is moved to the use position and the blood purification treatment is performed (S1).

On the basis of the detection signal from the detecting device S, it is determined whether or not the hanger portion 2b of the holding device 2 is moved from the use position (S2). If the hanger portion 2b is not moved from the use position, the blood purification treatment is continued. If the hanger portion 2b is moved from the use position, the processing proceeds to S3, and the control relating to the blood purification treatment (for example, the driving of the peristaltic pumps P1 to P4 and the measurement by the measuring devices g) is stopped.

After that, on the basis of the detection signal from the detecting device S, it is determined whether or not the hanger portion 2b of the holding device 2 is moved to the use position (S4). If the hanger portion 2b is not moved to the use position, the control relating to the blood purification treatment remains stopped. If the hanger portion 2b is moved to the use position, the processing proceeds to S5, and the control relating to the blood purification treatment (for example, the driving of the peristaltic pumps P1 to P4 and the measurement by the measuring devices g) is resumed.

Since the above embodiment has the restricting device 6 that restricts the attachment and detachment of the container bags (B1 to B3) to and from the attachment portions 2c when the hanger portion 2b is in the use position, inadvertent replacement of the container bags (B1 to B3) attached to the hanger portion 2b can be avoided. Inadvertent replacement of the container bags (B1 to B3) is physically restricted when the hanger portion 2b is in the use position. Therefore, if the measured values of the measuring devices (g) are abnormal when the hanger portion 2b is in the use position, it is mainly caused by a problem with the blood purification apparatus 1, such as damage to the container bags (B1 to B3). Therefore, a false alarm can be prevented.

In particular, the restricting device 6 (the same goes for the restricting device 7) according to this embodiment is a shielding plate that is fixed to the apparatus main body A and that covers and shields the attachment portions 2c only when the hanger portion 2b is in the use position. Therefore, inadvertent replacement of the container bags (B1 to B3) when the hanger portion 2b is in the use position can be reliably avoided, and the configuration of the hanger portion 2b can be simplified.

Next, a blood purification apparatus according to a second embodiment of the present invention will be described.

The blood purification apparatus according to this embodiment is, as with the first embodiment, for providing a patient with blood purification treatment, and, as shown in FIGS. 15 to 18, includes a holding device 10 including a main body portion 10a, a hanger portion 10b that has attachment portions 10c to which container bags (B1 to B3) can be attached, and that is movable between a use position in which the container bags (B1 to B3) are used (see FIGS. 15 and 16) and a replacement position in which the container bags (B1 to B3) are replaced (see FIGS. 17 and 18), and measuring devices g capable of measuring the weights of the container bags (B1 to B3) held by the hanger portion 10b (see FIG. 13). The description of the same configuration as that of the first embodiment (particularly the configuration of the apparatus main body A) will be omitted.

The main body portion 10a movably supports the hanger portion 10b, and includes, as with the first embodiment, a shaft portion L for swinging the hanger portion 10b, and a detecting device S, which is a sensor capable of detecting that the shaft portion L is in a predetermined position. That is, when the hanger portion 10b is under the main body portion 10a as shown in FIGS. 15 and 16, the hanger portion 10b is in the "use position." When the hanger portion 10b is swung about the shaft portion L, and the hanger portion 10b is in a position distant from the main body portion 10a as shown in FIGS. 17 and 18, the hanger portion 10b is in the "replacement position."

The hanger portion 10b is a bar-like member one end of which is attached to the shaft portion L, and has attachment portions 10c formed at predetermined intervals. The attachment portions 10c are hooks from which the container bags (B1 to B3) can be hung and that can hold them, and the measuring devices g are disposed at the respective proximal ends thereof. The measuring devices g are load meters that measure applied loads, and measure the weights of the container bags (B1 to B3) hung from the attachment portions 10c (the total weights of the container bags and the contents), and can transmit the measured values as electric signals to the control device H.

The holding device 10 according to this embodiment has a restricting device 11 that restricts the attachment and detachment of the container bags (B1 to B3) to and from the attachment portions 10c when the hanger portion 10b is in the use position. The restricting device 11 is a shielding plate that is attached to the hanger portion 10b and that is movable between a first position in which the attachment portions 10c are shielded (see FIGS. 15 and 16) and a second position in which the attachment portions 10c are open (see FIGS. 17 and 18), and is movable from the first position to the second position only when the hanger portion 10b is in the replacement position.

More specifically, the restricting device 11 according to this embodiment is formed, for example, by pressing a metal plate material into a substantially U shape, so as to have an upper surface portion 11b, and a flange portion 11c, and swings about shafts 11a formed on both end faces of the hanger portion 10b, and is movable between the first position and the second position. When the restricting device 11 is in the first position, as shown in FIG. 16, the upper surface portion 11b and the flange portion 11c of the restricting device 11 cover and shield the attachment portions 10c formed in the hanger portion 10b and restrict the attachment and detachment of the container bags (B1 to B3) to and from the attachment portions 10c (physically restrict the attachment and detachment). When the restricting device 11 is swung to the second position with the hanger portion 10b in the replacement position, as shown in FIG. 18, the attachment and detachment of the container bags (B1 to B3) to and from the attachment portions 10c are allowed. If, when the hanger portion 10b is in the use position, one tries to move the restricting device 11 from the first position to the second position, the restricting device 11 interferes with the main body portion 10a over it and its movement is restricted.

Since the above embodiment has, as with the first embodiment, the restricting device 11 that restricts the attachment and detachment of the container bags (B1 to B3) to and from the attachment portions 10c when the hanger portion 10b is in the use position, inadvertent replacement of the container bags (B1 to B3) attached to the hanger portion 10b can be avoided. Inadvertent replacement of the container bags (B1 to B3) is physically restricted when the hanger portion 10b is in the use position. Therefore, if the measured values of the measuring devices g are abnormal when the hanger portion 10b is in the use position, it is mainly caused by a problem with the blood purification apparatus 1, such as damage to the container bags (B1 to B3). Therefore, a false alarm can be prevented.

In particular, the restricting device 11 according to this embodiment is a shielding plate that is attached to the hanger portion 10b and that is movable between a first position in which the attachment portions 10c are shielded and a second position in which the attachment portions 10c are open, and is movable from the first position to the second position only when the hanger portion 10b is in the replacement position. Therefore, inadvertent replacement of the container bags (B1 to B3) when the hanger portion 10b is in the use position can be reliably avoided, and the restricting device 11 can be caused to follow the hanger portion 10b.

Although embodiments have been described, the present invention is not limited to them. For example, the restricting device (6, 11) that restricts the attachment and detachment of the container bags (B1 to B3) to and from the attachment portions (2c, 10c) when the hanger portion (2b, 10b) is in the use position is not limited to the shielding plates in the above-described embodiments, but may be, for example, a bar-like restricting device 12 that is swingably attached to an attachment portion (f) (hook) capable of holding a container bag as shown in FIG. 19.

In this case, the weight of the container bag attached to the attachment portion (f) can be measured by a measuring device (g). When the hanger portion of the holding device is in the use position, as shown in (a) of the figure, the swing of the restricting device 12 is restricted by the apparatus main body M or the like, and the replacement (attachment and detachment) of the container bag to and from the attachment portion (f) is restricted by the restricting device 12. When the hanger portion of the holding device is in the replacement position, as shown in (b) of the figure, the restricting device 12 swings about a shaft 12a and the restriction by the restricting device 12 is removed, and the replacement (attachment and detachment) of the container bag to and from the attachment portion (f) is allowed. The restricting device 12 in this case has a hole 12b formed at a predetermined position thereof. In the restricting state, the hole 12b fits on the distal end of the attachment portion f as shown in (a) of the figure.

If a blood purification apparatus includes a holding device including a hanger portion including an attachment portion to which a container bag can be attached and that is movable between a use position in which the container bag is used and a replacement position in which the container bag is replaced, a measuring device capable of measuring the weight of the container bag held by the hanger portion, and a restricting device that restricts the attachment and detachment of the container bag to and from the attachment portions when the hanger portion is in the use position, the blood purification apparatus can also be applied to those which have different outer shapes or other additional functions.

REFERENCE SIGN LIST 1 blood purification apparatus
2 holding device
3 display
4 clamping device
5 holding device
6 restricting device
7 restricting device
8a arterial blood circuit
8b venous blood circuit
9 dialyzer (blood purifier)
10 holding device
11 restricting device
12 restricting device
B1 to B4 container bag

The invention claimed is:
1. A blood purification apparatus comprising:
a holding device that holds a plurality of container bags containing a liquid for blood purification treatment, including a dialysate, substitution fluid, or anticoagulant, the blood purification apparatus configured to perform a blood purification treatment using the liquid in the at least one of the plurality of container bags based on control via a controller,
wherein the holding device includes:
a hanger portion including a plurality of attachment portions to which the plurality of container bags can be attached, the hanger portion being movable between a use position in which the plurality of container bags are used and a replacement position in which the plurality of container bags are replaced;
a load meter that measures a weight of the plurality of container bags held by the hanger portion; and
a restricting device that restricts attachment and detachment of the plurality of container bags to and from the plurality of attachment portions when the hanger portion is in the use position, wherein the restricting device is a shielding plate that covers and shields the plurality of attachment portions and restricts attachment and detachment of the plurality of container bags to and from the plurality of attachment portions; and
wherein the holding device includes a fixed main body portion that receives a shaft connected to the hanger portion so that the hanger portion pivots between the use position and the replacement position about an axis of the shaft.

2. The blood purification apparatus according to claim 1, wherein the shielding plate is fixed to an apparatus main body and that covers and shields the plurality of attachment portions only when the hanger portion is in the use position.

3. The blood purification apparatus according to claim 2, further comprising a position sensor that detects if the hanger portion is in the use position.

4. The blood purification apparatus according to claim 2, further comprising a detecting device that detects if the hanger portion is in the use position, and wherein when, during the blood purification treatment, the detecting device does not detect that the hanger portion is in the use position, the controller stops the blood purification treatment by stopping the driving of the one or more peristaltic pumps of the blood purification apparatus and stopping measurement of the load meter.

5. The blood purification apparatus according to claim 2, wherein the shielding plate comprises a substantially U-shaped body and a flange, and wherein the flange abuts the plurality of attachment portions in the use position to prevent removal of the plurality of container bags.

6. The blood purification apparatus according to claim 1, wherein the shielding plate is attached to the hanger portion and that is movable between a first position in which the plurality of attachment portions are shielded and a second position in which the plurality of attachment portions are open, the shielding plate being movable from the first position to the second position only when the hanger portion is in the replacement position.

7. The blood purification apparatus according to claim 6, further comprising a position sensor that detects if the hanger portion is in the use position.

8. The blood purification apparatus according to claim 6, further comprising a detecting device that detects if the hanger portion is in the use position, and wherein when, during the blood purification treatment, the detecting device does not detect that the hanger portion is in the use position, the controller stops the blood purification treatment by stopping the driving of the one or more peristaltic pumps of the blood purification apparatus and stopping measurement of the load meter.

9. The blood purification apparatus according to claim 1, further comprising a position sensor that detects if the hanger portion is in the use position.

10. The blood purification apparatus according to claim 9, wherein when the position sensor detects that the hanger portion is not in the use position, a warning is output to a display of the blood purification apparatus.

11. The blood purification apparatus according to claim 9, wherein when the position sensor detects that the hanger portion is not in the use position, a warning signal is output by a speaker, a warning light, or both.

12. The blood purification apparatus according to claim 1, further comprising a detecting device that detects if the hanger portion is in the use position, and wherein when, during the blood purification treatment, the detecting device does not detect that the hanger portion is in the use position, the controller stops the blood purification treatment by stopping the driving of the one or more peristaltic pumps of the blood purification apparatus and stopping measurement of the load meter.

13. The blood purification apparatus according to claim 12, wherein when, after the blood purification treatment is stopped, the detecting device detects that the hanger portion is in the use position, the blood purification treatment is resumed.

14. The blood purification apparatus according to claim 1, wherein the blood purification apparatus comprises a first holding device and a second holding device, and the first holding device and the second holding device each are configured to hold separate container bags.

15. The blood purification apparatus according to claim 1, wherein the restricting device is movable between a first position in which the plurality of attachment portions are shielded and a second position in which the plurality of attachment portions are unshielded.

16. The blood purification apparatus according to claim 15, wherein the restricting device is only movable when the hanger portion is in the replacement position.

17. The blood purification apparatus according to claim 1, wherein the hanger portion pivots between the use position and the replacement position by rotating the shaft within the main body portion about the axis of the shaft.

18. The blood purification apparatus according to claim 1, wherein the shaft includes a protrusion that is detected by a position sensor when the hanger portion is in the use position, the position sensor being secured within the main body portion.

19. The blood purification apparatus according to claim 1, wherein the hanger portion is a bar-like member and a first end of the hanger portion is attached to the shaft.

20. The blood purification apparatus according to claim 1, wherein each of the plurality of attachment portions is a hook and the load meter is positioned near a proximal end of the hook where the hook is secured to the hanger portion.

* * * * *